United States Patent [19]

Ponsford

[11] Patent Number: 4,505,894
[45] Date of Patent: Mar. 19, 1985

[54] THERAPEUTIC COMPOUNDS CONTAINING β-LACTAMS

[75] Inventor: Roger J. Ponsford, Horsham, England

[73] Assignee: Beecham Group Limited, England

[21] Appl. No.: 412,591

[22] Filed: Aug. 30, 1982

Related U.S. Application Data

[60] Continuation of Ser. No. 208,150, Nov. 19, 1980, abandoned, which is a continuation of Ser. No. 930,574, Aug. 3, 1978, abandoned, which is a division of Ser. No. 796,712, Jan. 24, 1977, Pat. No. 4,428,958.

[30] Foreign Application Priority Data

Jan. 31, 1976 [GB] United Kingdom ............... 03892/76
May 8, 1976 [GB] United Kingdom ............... 19002/76

[51] Int. Cl.³ .............................................. A61K 35/00
[52] U.S. Cl. ................................................... 424/114
[58] Field of Search ......................................... 424/114

Primary Examiner—Jerome D. Goldberg
Attorney, Agent, or Firm—Jacobs & Jacobs

[57] ABSTRACT

Compounds of the formula

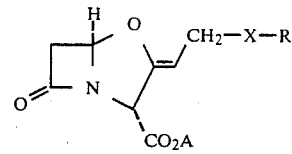

wherein X is S, SO or $SO_2$ and R is an inert hydrocarbon of up to 20 carbon atoms which will not lead to rapid degradation of the above compound unsubstituted or substituted and A is a group such and $CO_2A$ represents a carboxylic acid group or a salt or ester thereof, are useful for their antibacterial activity and for their β-lactamase inhibitory activity.

98 Claims, No Drawings

THERAPEUTIC COMPOUNDS CONTAINING β-LACTAMS

CROSS-REFERENCE

This is a continuation of Ser. No. 208,150 now abandoned filed Nov. 19, 1980 which is a continuation of Ser. No. 930,574 filed Aug. 3, 1978, now abandoned, which is itself a divisional of Ser. No. 761,712 filed Jan. 24, 1977, now U.S. Pat. No. 4,428,958.

The present invention relates to new β-lactam containing compounds, to the process for their preparation and to pharmaceutical compositions containing them.

Belgian Pat. No. 827926 discloses inter alia clavulanic acid which has the formula (I):

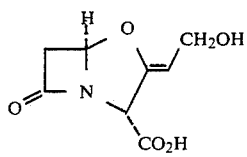

and its salts and esters. It has now been discovered that such compounds can be converted into thioethers which possess β-lactamase inhibitory properties and a degree of antibacterial activity.

The present invention provides the compounds of the formula (II):

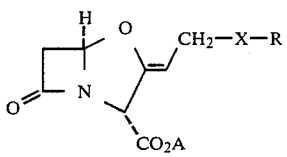

wherein X is S, SO or $SO_2$ and R is an organic group of up to 20 carbon atoms and A is a group such that $CO_2A$ represents a carboxylic acid group or a salt or ester thereof.

The group R will be inert, that is the inclusion of the group R will not lead to the rapid degradation of the compound of the formula (II).

Suitable organic groups R for inclusion in the compounds of the formula (II) include hydrocarbon groups and hydrocarbon groups substituted by halogen and/or groups of the sub-formulae $OR^1$, $O.COR^1$, $CO.R^1$, $CO_2R^1$, $NHR^1$, $NR^1R^2$, $NH.CO.R^1$, $NR^2COR^1$, $NHCO_2R^1$, $NR^2CO_2R^1$ wherein $R^1$ is a hydrogen atom or a hydrocarbon group of up to 8 carbon atoms and $R^2$ is an alkyl group of 1–3 carbon atoms.

Suitable hydrocarbon groups include alkyl groups especially those of up to 6 carbon atoms.

One particularly suitable sub-group of compounds of the formula (II) are those wherein R is a group $CH_2R^3$ wherein $R^3$ is a hydrogen atom or an alkyl group of up to 5 carbon atoms or a naphthyl group or a phenyl group optionally substituted by halogen or hydroxyl or amino, or a group of the formula $R^4$, $OR^4$ or $NR^4R^5$ where $R^4$ is an alkyl or acyl group of up to 3 carbon atoms and $R^5$ is a hydrogen atom or an alkyl group of up to 4 carbon atoms.

A further suitable sub-group of compounds of the formula (II) are those wherein R is a group $CR^6R^7R^8$ wherein $R^6$ and $R^7$ are independently alkyl groups of up to 3 carbon atoms or a phenyl group optionally substituted by halogen or a group of the formula $R^9$ or $OR^9$ where $R^9$ is an alkyl group of up to 3 carbon atoms; and $R^8$ is a hydrogen atom or an alkyl group of up to 3 carbon atoms or a phenyl group optionally substituted by halogen or a group of the formula $R^{10}$ or $OR^{10}$ where $R^{10}$ is an alkyl group of up to 3 carbon atoms. Another suitable sub-group of compounds of the formula (II) are those wherein R is a group $R^{11}$ which is an optionally substituted heteroaromatic group of 5- or 6-ring atoms. Suitable groups $R^{11}$ include triazole, tetrazole, thienyl, thiazole, thiadiazole, thiatriazole, oxazole, isoxazolyl, oxadiazole, pyridyl, pyridazinyl, pyrimidinyl and the like optionally substituted. Suitable substituents for such groups include alkyl groups of up to 3 carbon atoms or less preferably such groups themselves substituted by a $CONH_2$ or $CO_2H$ group or the like.

Other suitable groups R include those described in West German Offenlegungsschrift No. 2503335 as suitable for inclusion at the 3-position of 3-thiomethyl cephalosporins, namely lower alkyl, lower alkenyl or lower alkinyl with up to 7, preferably up to 4, carbon atoms, or a heterocyclic radical, bonded to the $CH_2$ via a ring carbon, which contains 1 to 4 ring nitrogen atoms and optionally a further ring hetero-atom from the group of hydrogen and sulphur, with such a radical optionally being substituted by lower alkyl with up to 4 carbon atoms. A heterocyclic radical R defined as above is, for example, an optionally substituted, bicyclic, but preferably monocyclic, heterocyclic radical, which has aromatic properties or can be partially saturated. Examples of substituents in heterocyclic radicals R are lower alkyl, especially methyl, hydroxy-lower alkyl, for example hydroxymethyl, cycloalkyl, for example cyclopentyl or cyclohexyl, aryl, such as phenyl optionally substituted by halogen, for example chlorine or nitro, aryl-lower alkyl, such as benzyl which is optionally substituted, for example by a phenyl radical, or heterocyclyl, such as furyl, thienyl or oxazolyl, or functional groups, such as halogen, optionally substituted amino, such as amino optionally mono-substituted or disubstituted by lower alkyl, nitro, lower alkoxy, or optionally functionally modified carboxyl, such as carboxyl, esterified carboxyl, such as lower alkoxycarbonyl, optionally substituted, such as N-mono- or N,N-di-lower alkylated carbamoyl, or cyano, as well as oxo or oxido it being possible for one or more such substituents to be present, the substituents above all being bonded to ring carbon atoms but also, especially in the case of lower alkyl and oxido, to ring nitrogen atoms.

Heterocyclic radicals R are above all mono-cyclic five-membered, diazacyclic, triazacyclic, tetrazacyclic, thiazacyclic, thiadiazacyclic, thiatriazacyclic, oxazacyclic or oxadiazacyclic radicals of aromatic character which are optionally substituted, for example which contain the abovementioned substituents, especially lower alkyl, for example methyl, or corresponding radicals which are optionally substituted, for example which contain the abovementioned substituents, and have a fused-on benzene ring, such as benzodiazacyclic and benzooxacyclic radicals. Such radicals R may also be monocyclic, six-membered monoaxacyclic or diazacyclic radicals of aromatic character which are optionally substituted, for example which contain the abovementioned substituents, above abl oxido, or corresponding partially saturated radicals which are optionally substituted, for example which contain the abovementioned substituents, above all oxo, or they may be bicyclic triazacyclic or tetrazacyclic radicals of aromatic character which are optionally substituted, for example which contain the abovementioned substituents, or corresponding partially saturated radicals which are optionally substituted, for example which contain the abovementioned substituents, above all oxo.

Preferred monocyclic, five-membered heterocyclic radicals R or corresponding benzoheterocyclic radicals R are inter alia, imidazolyl, for example 2-imidazolyl, triazolyl which is optionally substituted by lower alkyl and/or phenyl, for example s-triazol-2-yl, 4-methyl-3-triazol-2-yl, 1H-1,2,4-triazol-5-yl, 4,5-dimethyl-4H-1,2,4-triazol-3-yl or 4-phenyl-4H-1,2,4-triazol-3-yl, tetrazoyl which is optionally substituted by lower alkyl, phenyl or halogenophenyl, for example 1H-5-tetrazolyl, 1-methyl-1H-5-tetrazoyl, 1-phenyl-1H-5-tetrazolyl or 1-(4-chlorophenyl)-1H-5-tetrazoyl, thiazoyl which is optionally substituted by lower alkyl or thienyl, for example 2-thiazolyl, 4-(2-thienyl)-2-thiazoyl or 4,5-dimethyl-2-thiadiazol, thiadiazoyl which is optionally substituted by lower alkyl, for example 1,3,4-thiadiazaol-2-yl, 2-methyl-1,3,4-thiadiazol-5-yl or 1,2,4-thiadiazol-5-yl, thiatriazolyl, for example 1,2,3,4-thiatriazoyl-5-yl, oxazolyl or isoxazolyl which is optionally substituted by lower alkyl or phenyl, for example 5-oxazolyl, 4-methyl-5-oxazolyl, 2-oxazolyl, 4,5-diphenyl-2-oxozolyl or 3-methyl-5-isaoxazolyl, oxadiazolyl which is optionally substituted by lower alkyl, phenyl, nitrophenyl or thienyl, for example 1,2,4-oxadiazol-5-yl, 2-methyl-1,3,4-oxadiazol-5-yl, 2-phenyl-1,3,4-oxadiazol-5-yl, 5-(4-nitrophenyl)-1,3,4-oxadiazol-5-yl, benzimidazolyl which is optionally substituted by halogen, for example 2-benzimidazolyl or 5-chloro-2-benzimidazolyl, or benzoxazolyl which is optionally substituted by halogen or nitro, for example 2-benzooxazolyl, 5-nitro-2-benzoxazolyl or 5-chloro-2-benzoxazolyl.

Preferred monocyclic, six-membered heterocyclic radicals R or corresponding partially saturated radicals are, inter alia, 1-oxido-pyridyl which is optionally substituted by halogen, for example 1-oxido-2-pyridyl or 4-chloro-1-oxido-2-pyridyl, N-oxido-pyridazinyl which is optionally substituted by lower alkyl, lower alkoxy or halogen, for example 2-oxido-6-pyridazinyl, 2-chloro-1-oxido-6-pyridazinyl, 3-methyl-2-oxido-6-pyridazinyl, 3-methoxy-1-oxido-6-pyridazinyl, 3-ethoxy-1-oxido-6-pyridazinyl 3-n-butoxy-1-oxido-6-pyridazinyl or 3-O-ethylhexyloxyl-1-oxido-6-pyridazinyl, or 2-oxo-1,2-dihydro-pyrimidinyl which is optionally substituted by lower alkyl, amino, di-lower alkylamino or carboxyl, for example 2-oxo-1,2-dihydro-4-pyrimidinyl, 6-methyl-2-oxo-1,2-dihydro-4-pyrimidinyl, 5-methyl-2-oxo-1,2-dihydro-4-pyrimidinyl, 6-amino-2-oxo-1,2-dihydro-4-pyrimidinyl, 6-dimethylamino-2-oxo-1,2-dihydro-4-pyrimidinyl, 5-carboxy-2-oxo-1,2-dihydro-4-pyrimidinyl or 6-carboxy-2-oxo-1,2-dihydro-4-pyrimidinyl.

Preferred heterocyclic bicyclic optionally partially saturated radicals R are, inter alia, triazolopyridyl, for example 3-s-triazolo[4,3-a]pyridyl or 5-v-triazolo[4,5-b]pyridyl or purinyl which is optionally substituted by halogen and/or lower alkyl, for example 2-purinyl, 6-purinyl or 8-chloro-2-methyl-6-purinyl, and also 2-oxo-1,2-dihydropurinyl, for example 2-oxo-1,2-dihydro-6-purinyl.

R may represent methyl or thiadiazolyl which is optionally substituted by lower alkyl, for example methyl, and is bonded to the thio sulphur atom via a ring carbon atom, for example 1,3,4-thiadiazaol-2-yl, 5-methyl-1,3,4-thiadiazol-2-yl or 5-methyl-1,2,4-thiadazol-2-yl, or tetrazoyl which is similarly substituted and bonded, for example 1-methyl-5-tetrazolyl, or N-oxidopyridazinyl which is optionally substituted by lower alkyl, for example methyl, lower alkoxy, for example methoxy, or halogen, for example chlorine, and is bonded to the thio sulphur atom via a ring carbon atoms, for example 3-methyl-2-oxido-6-pyridazinyl, 3-methoxy-1-oxido-6-pyridazinyl or 3-chloro-1-oxido-6-pyridazinyl.

Yet another suitable sub-group of compounds of the formula (II) are those wherein R is a phenyl group optionally substituted by a group of the sub-formula $OR^1$, $O.COR^1$, $COR^1$, $CO_2R^1$ as hereinbefore defined or by chlorine, bromine, fluorine or the like.

One group of particularly suitable compounds of the formula (II) are those of the formula (III),

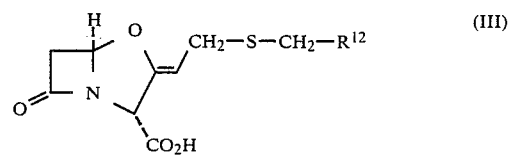

and pharmaceutically acceptble salts thereof wherein $R^{12}$ is a phenyl group optionally substituted by fluorine, chlorine, bromine or $OR^{13}$, $O.CO.R^{13}$, $COR^{13}$, $CO_2R^{13}$ where $R^{13}$ is a hydrocarbon group of up to 8 carbon atoms.

Other particularly suitable compounds of the formula (II) are the sulphoxides and sulphones corresponding to the sulphides of formula (III).

Another group of particularly suitable compounds of the formula (II) are those of the formmula (IV):

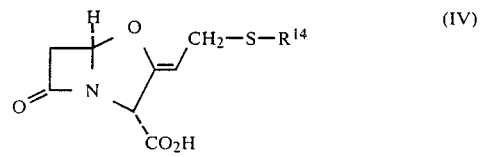

and pharmaceutically acceptable salts thereof wherein $R^{14}$ is a 5-membered heterocyclic group optionally substituted by an alkyl group of up to 3 carbon atoms.

Suitable groups $R^{14}$ include those which contain 3 or 4 heteroatoms at least two of which are nitrogen atoms.

Particularly suitable groups $R^{14}$ include those of the sub-formulae (a) and (b):

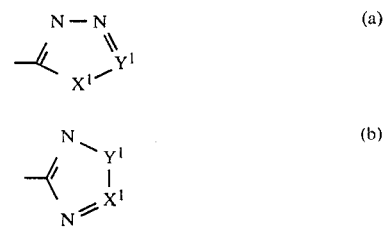

wherein $X^1-Y^1$ represents a $S-N(CH_3)$, $O-N(CH_3)$, $N-N(CH_3)$, $N-CH_2$, $O-CH_2$ or $S-CH_2$ group.

A further group of particularly suitable compounds of the formula (II) are those of the formula (V):

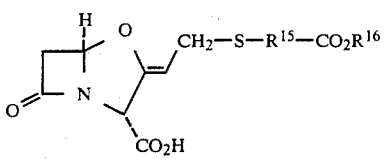

(V)

and pharmaceutically acceptable salts thereof wherein $R^{15}$ is a divalent hydrocarbon group of 1-8 carbon atoms and $R^{16}$ is a hydrogen atom or a hydrocarbon group of 1-8 carbon atoms.

Suitable groups $R^{15}$ include alkylene groups of 1-4 carbon atoms or an alkyl group of 1 or 2 carbon atoms substituted by a phenyl group.

Suitable groups $R^{16}$ include the hydrogen atom and alkylene groups of 1-4 carbon atoms or an alkylene group of 1 or 2 carbon atoms substituted by a phenyl group.

Other particularly suitable compounds of the formula (II) are those sulphoxides and sulphones corresponding to the sulphides of the formula (V).

From the foregoing it will be realised that suitable groups R include the methyl, ethyl, n-propyl, n-butyl, 2-methoxyethyl, 2-benzyloxymethyl, 2-ethoxyethyl, 3-methoxypropyl, benzyl, p-chlorobenzyl, p-methoxybenzyl, m-methoxybenzyl, p-methylbenzyl, phenyl, 4-fluorophenyl, 2-phenylethyl and the like groups.

Suitable groups A in the compounds of the formula (II) and equivalent groups in subsequently described compounds include hydrogen and salting ions such as the lithium, sodium, potassium, calcium, magnesium, ammonium and amine salts such as alkylamine, dialkylamine, trialkylamine, pyrrolidine and like salts.

Most suitably the group A represents a pharmaceutically acceptable alkali metal or alkaline earth metal ion.

The lithium salts of the compounds of this invention are frequently advantageous owing to their easy isolation and good storage properties.

The sodium and potassium salts (especially the sodium salts) of the compounds of this invention are advantageous because of the clear pharmaceutically acceptability of the sodium and potassium ions.

The salts of this invention are preferably crystalline. Further, since they are to be used as pharmaceutical agents or intermediates in the preparation of pharmaceutical agents it is preferable that they have the high degree of purity associated with pharmaceuticals.

Particularly suitable esters of the compounds of the formula (II) and subsequent formulae include those of the formulae (VI) and (VII):

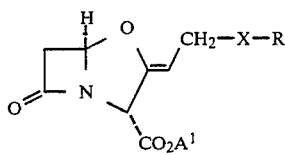

(VI)

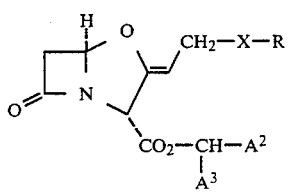

(VII)

wherein X and R are as defined in relation to formula (II) and $A^1$ is an alkyl group of 1-8 carbon atoms optionally substituted by halogen or a group of the formula $OA^4$, $OCOA^4$, $SA^4$, $SO_2A^4$ wherein $A^4$ is a hydrocarbon group of up to 6 carbon atoms; $A^2$ is a hydrogen atom, an alkyl group of up to 4 carbon atoms or a phenyl group optionally substituted by halogen or by a group $A^5$ or $OA^5$ where $A^5$ is an alkyl group of up to 6 carbon atoms; and $A^3$ is a phenyl group optionally substituted by halogen or by a group $A^5$ or $OA^5$ where $A^5$ is an alkyl group.

Benzyl and p-methoxybenzyl esters of the compounds of the formula (II) are particularly useful hydrogenolysable esters.

The present invention also provides a pharmaceutical composition which comprises a compound of this invention and a pharmaceutically acceptable carrier therefore.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials, such as diluents, binders, colours, flavours, preservatives, disintegrants and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt or ester thereof adapted for oral administration form a further preferred composition aspect of this invention.

Under certain conditions, the effectiveness of oral compositions of compounds of the formula (II) and their salts and esters can be improved if such compositions contain a buffering agent or an enteric coating agent such that the compounds of the invention do not have prolonged contact with highly acidic gastric juice. Such buffered or enterically coated compositions may be prepared in accordance with conventional pharmaceutical practice.

The compound of the formula (II) or its salt or ester may be present in the composition as sole therapeutic agent or it may be present together with other therapeutic agents such as a penicillin or cephalosporin. Suitable penicillins or cephalosporins for inclusion in such synergistic compositions include not only those known to be highly susceptible to β-lactamases but also those which have a degree of intrinsic resistance to β-lactamases. Thus, suitable β-lactam antibiotics for inclusion in the compositions of this invention include benzylpenicillin, phenoxymethylpenicillin, carbenicillin, methicillin, propicillin, ampicillin, amoxycillin, epicillin, ticarcillin, cyclacillin, cephaloridine, cephalothin, cefazolin, cephalexin, cefoxitin, cephacetrile, cephamandole, cephapirin, cephradine, cephaloglycine and other well known penicillins and cephalosporins or pro-drugs therefore such as hetacillin, metampicillin, the acetoxymethyl, pivaloyloxymethyl or phthalidyl esters of benzylpenicillin, ampicillin, amoxycillin or cephaloglycine or the phenyl, tolyl, or indanyl α-esters of carbenicillin or ticarcillin or the like.

Naturally if the penicillin or cephalosporin present in the composition is not suitable for oral administration then the composition will be adapted for parenteral administration.

When present in a pharmaceutical composition together with a penicillin or cephalosporin, the ratio of the compound of the formula (II) or its salt or ester present to penicillin or cephalosporin present may be from, over a wide range of ratios, for example, 1:10 to 3:1 and advantageously may be from 1:5 to 2:1 for example, 1:1 to 1:3.

The total quantity of antibacterial agent present in any unit dosage form will normally be between 50 and 1500 mg and will usually be between 100 and 1000 mg.

Compositions of this invention may be used for the treatment of infections of inter alia, the respiratory tract, the urinary tract and soft tissues in humans.

Compositions of this invention may also be used to treat infections of domestic animals such as mastitis in cattle.

Normally between 50 and 3000 mg of the compositions of the invention will be administered each day of treatment but more usually between 100 and 1000 mg of the compositions of the invention will be administered per day. However, for the treatment of severe systemic infections or infections of particularly intransigent organisms, higher doses may be used in accordance with clinical practice.

The penicillin or cephalosporin in synergistic compositions of this invention will normally be present up to or at approximately the amount conventionally used when that penicillin or cephalosporin is the sole therapeutic agent used in the treatment of infection.

Particularly favoured compositions of this invention will contain from 150-1000 mg of amoxycillin, ampicillin or a pro-drug (such as one of their salts, hydrates or in-vivo hydrolysable esters) therefore and from 50-500 mg of the compound of the formula (II) or a salt or in-vivo hydrolysable ester thereof and more suitably from 200-500 mg of amoxycillin, ampicillin or a pro-drug therefore and from 50-250 mg of the compound of the formula (II) or a salt or in-vivo hydrolysable ester thereof.

Amoxycillin trihydrate and the alkali metal salts of amoxycillin are particularly suitable for inclusion in the compositions of this invention.

The present invention also provides a process for the preparation of the compounds of the formula (II) which process comprises the reaction of an ester of clavulanic acid with a compound of the formula (VIII):

  (VIII)

wherein R is as defined in relation to formula (II) and thereafter preforming one or more of the following optional steps:
 (a) de-esterifying the thus produced ester to form the free or salted acid within formula (II);
 (b) re-esterifying the thus produced free or salted acid to yield a further ester within formula (II);
 (c) oxidizing the sulphide to a sulphoxide or sulphone.

Esters within formula (II) wherein X is S are first prepared by the reaction of a thiol of the formula (VIII) as defined with the corresponding ester of the compound of the formula (I) in the presence of an acid catalyst.

If the group R contains a reactive group such as an amino or a carboxylate function, these reactive groups may be protected in conventional manner prior to the operation of the above process and thereafter regenerated in conventional manner.

Suitably the catalyst is a Lewis acid catalyst such as boron trifluoride or its equivalent such as a boron trifluoride etherate, for example $BF_3.O(C_2H_5)_2$.

The preceding reaction normally takes place in a solvent inert under the reaction conditions (eg. dry and non-hydroxylic) such as chloroform, dichloromethane, tetrahydrofuran, dioxane or the like.

Most suitably the reaction takes place at a depressed or non-elevated temperature, for example $-80°$ to $+30°$ C., and preferably at a depressed temperature, for example $-50°$ to $0°$ C.

Those esters within formula (II) wherein X is SO or $SO_2$ can be prepared from the corresponding compound wherein X is S by mild oxidation.

Such reactions may take place at an ambient or depressed temperature, for example at $-20°$ to $+20°$ C., more suitably at $-12°$ to $+5°$ C., for example at about $0°$ C.

The oxidation is best brought about using an organic per-acid as the oxidizing agent. Suitable acids include m-chloroperbenzoic acid and equivalent reagents. Use of one equivalent of the oxidizing agent leads to a compound of the formula (II) wherein X is SO whereas the use of two equivalents of the oxidizing agent leads to a compound of the formula (II) wherein X is $SO_2$.

It is normal to carry out the oxidation in an inert solvent such as methylene chloride or the like.

Acids and salts within formula (II) may with difficulty be prepared from hydrogenolysable esters such as the benzyl and methoxybenzyl esters within formula (II) by hydrogenation using a medium or low pressure of hydrogen in the presence of a transition metal catalyst such as 10% palladium on charcoal wherein the weight of catalyst to thioether is about 1:3. Suitable solvents include tetrahydrofuran and ethanol. If a base is included the initially produced acid is converted to a salt which is then isolated.

Salts within formula (II) wherein X is S may be prepared from esters within formula (II) by very mild basic hydrolysis, for example by hydrolysis in an aqueous solution maintained at pH 7 to 9 by the slow addition of base. Suitable bases include lithium hydroxide, sodium hydroxide and their chemical equivalents.

Suitable esters for hydrolysis include the methyl, methoxymethyl and the benzyl esters, the methoxymethyl ester being preferred.

Acids within formula (II) may be prepared by the careful acidification of a corresponding salt such as the sodium salt.

Salts within formula (II) may also be prepared by salt exchange in conventional manner; for example a solution of the lithium salt in water may be passed through a bed of ion exchange resin in the sodium form (e.g. Amberlite 120; a sodium salt of a sulphonated polystyrene divinyl benzene co-polymer) in about ten-fold excess until elution is complete; the resulting sodium salt may be obtained by freeze drying or the like. Similarly a sodium salt may be converted to a lithium salt or to a potassium salt in similar manner.

The following Examples illustrate the invention.

EXAMPLE 1

Benzyl3-(2-thiobenzylethylidene)-7-oxo-4-oxa-1-azabicyclo[3,2,0]heptane-2-carboxylate

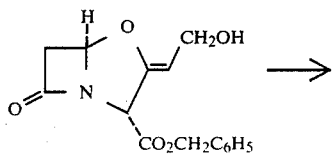

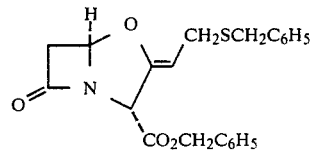

Benzyl clavulanate (500 mg) was dissolved in methylene chloride (50 ml) and cooled to −30° C. Boron trifluoride etherate (7 drops) was added at −30° C. followed by a solution of benzyl mercaptan (220 mg) in methylene chloride (5 ml) dropwise at −30° C. The solution was stirred at −30° C. to 0° C. for 1½ hours, washed with 3% sodium bicarbonate solution (3×25 ml) and the extract dried over MgSO$_4$. Evaporation of the solvent and chromatography yielded the title compound (150 mg; 25%) as a colourless oil.

I.r. (CHCl$_3$): 1800, 1745, 1690 cm$^{-1}$;

N.m.r. (CDCl$_3$): 3.00 (1H,d,J=17 Hz, 6β-C$\underline{H}$); 3.52 (1H,dd,J=17 Hz, J'=2.5 Hz, 6α-C$\underline{H}$); 3.20 (2$\underline{H}$, d, J=8 Hz, C$\underline{H_2}$SB$_2$); 3.77 (2H, s, SC$\underline{H_2}$Ph); 4.77 (1H, t, J=8 Hz, =C$\underline{H}$—CH$_2$); 5.18 (1H, brs, 3-C$\underline{H}$); 5.30 (2H, s, CO$_2$C$\underline{H_2}$Ph); 5.72 (1H, d, J=2.5 Hz, 6-C$\underline{H}$); 7.40 and 7.50 (10H, two singlets, SCH$_2$Ph and CO$_2$CH$_2$Ph). M.w. (mass spectrometry) 395.

| β-Lactamase Inhibition I$_{50}$ (μg/ml) | |
|---|---|
| Escherichia coli | 0.3 |
| Klebsiella aerogenes E70 | 0.2 |
| Staphylococcus aureus Russell | <0.07 |
| Pseudomonas aeruginosa A. | 1.8 |
| Pseudomonas dalgleish | 0.76 |
| Citrobacter mantio | 24 |

EXAMPLE 2

Benzyl3-(2-benzylsulphinylethylidene)-7-oxo-4-oxa-1-azabicyclo[3,2,0]heptane-2-carboxylate

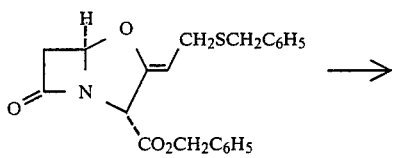

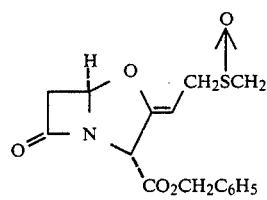

Benzyl3-(2-benzylthioethylidene)-7-oxo-4-oxa-1-azabicyclo[3,2,0]heptane-2-carboxylate (39.5 mg) was dissolved in methylene chloride (5 ml) and treated with m-chloroperbenzoic acid (19 mg) at 0° C. The solution was stirred at 0° C. for ½ hour and washed with 3% bicarbonate solution (3×5 ml). The solvent was evaporated and the gum chromatographed to yield the title product as a mixture of R and S sulphoxides (30 mg; 73%).

I.r. (CHCl$_3$): 1800, 1750, 1700 cm$^{-1}$;

N.m.r. (CDCl$_3$): 3.10 (1H, d, J=17 Hz, 6β-C$\underline{H}$); 3.50 (2H, br.d., J=8 Hz, =CH—C$\underline{H_2}$—); 3.62 (1H, dd, J=17 Hz, J'=2.5 Hz, 6α-C$\underline{H}$); 3.87 and 3.97

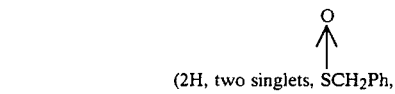

(2H, two singlets, SCH$_2$Ph, R and S sulphoxides); 4.86 (1H,. br.t., J=8 Hz, =C$\underline{H}$—CH$_2$—); 5.26 (1H, brs., 3-O$\underline{H}$; 5.33 (2H, s, CO$_2$C$\underline{H_2}$Ph); 5.83 (1H, d, J=2.5 Hz, 5-C$\underline{H}$); 7.48δ

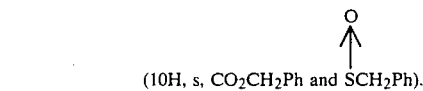

(10H, s, CO$_2$CH$_2$Ph and SCH$_2$Ph).

[α]$_D^{20}$ = +7.2° (c=0.94; MeOH).

| Antibacterial Activity In Vitro (μg/ml) | |
|---|---|
| Staphylococcus aureus Oxford | 62 |
| Staphylococcus aureus Russell | 62 |
| β-Lactamase Inhibition I$_{50}$ (μg/ml) | |
| Escherichia coli JT4 | 0.07 |
| Klebsiella aerogenes E70 | 0.8 |
| Staphylococcus aureus Russell | 0.16 |
| Pseudomonas aeruginosa A. | 0.6 |
| Citrobacter mantio | 0.26 |

EXAMPLE 3

Methyl3-[2-(1-methyl-1,2,3,4-tetrazol-5-yl)thioethylidene]-7-oxo-4-oxa-1-azabicyclo[3,2,0]heptane-2-carboxylate

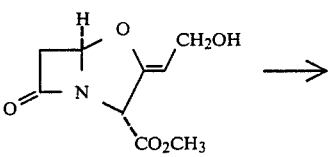

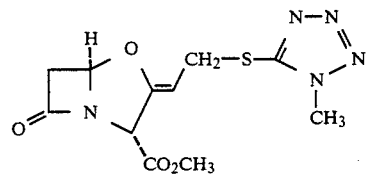

To methyl clavulanate (213 mg) in dichloromethane (10 ml) at −20° C. was added boron trifluoride etherate (5 drops) followed by 1-methyl-1,2,3,4-tetrazol-5-thiol (120 mg). The reaction mixture was stirred for 2 hours during which period the temperature was gradually allowed to reach −10° C. The solution was washed with aqueous sodium bicarbonate solution (3%, 3×10 ml). The organic phase was dried and the solvent removed by evaporation. Chromatography of the crude material yielded the title compound (approximately 40% yield).

I.r. (CHCl$_3$): 1800, 1750, 1690 cm$^{-1}$.

N.m.r. (CDCl$_3$): 3.04 (1H, d, J=17 Hz, 6$\beta$-CH); 3.50 (1H, dd, J=17 Hz, J'=2.5 Hz, 6$\alpha$-CH); 3.73 (3H, s, CO$_2$CH$_3$); 3.88 (3H, s, N—CH$_3$); 3.97 (2H, d, J=8 Hz, =CH—CH$_2$); 4.92 (1H, br.t, =CH—CH$_2$); 5.00 (1H, br.s, 3-CH); 5.72$\delta$ (1H, d, J=2.5 Hz, 5-CH). $[\alpha]_D^{21}$=+13° (c=1.34, MeOH).

The approximate $\beta$-lactamase inhibition I$_{50}$ values in $\mu$g/ml for the title compound were as follows:

| Escherichia coli JT4 | 0.02 |
| Klebsiella aerogenes E70 | >>1.0 |
| Staphylococcus aureus Russell | 0.21 |
| Proteus mirabilis C889 | 0.56 |
| Pseudomonas aeruginosa A | 0.035 |
| Pseudomonas dalgleish | 0.08 |
| Enterobacter P99 | 0.01 |

EXAMPLE 4

Methyl 3-(2-thiobenzylethylidene)-7-oxo-4-oxa-1-azabicyclo[3,2,0]heptane-2-carboxylate

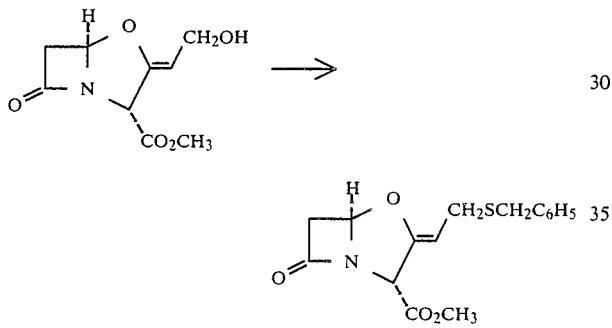

Methyl clavulanate (1 g) was dissolved in dry methylene dichloride (50 ml) and cooled to −30° C. Borontrifluoride etherate (15 drops) was added followed by benzyl mercaptan (620 mg) in methylene chloride (10 ml). The mixture was stirred at −30° C. to −10° for 2 hours and washed with 3% sodium bicarbonate solution (3×50 ml), dried over magnesium sulphate and the solvent evaporated to yield a yellow oil. Chromatography provided the title compound as a light yellow oil (219 mg; 20%).

I.r. (CHCl$_3$): 1800, 1750, 1690 cm$^{-1}$;

N.m.r. (CDCl$_3$): 2.93 (1H, d, J=17 Hz, 6$\beta$-CH); 3.15 (2H, d, J=8 Hz, =CH—CH$_2$); 3.45 (1H, dd, J=17 Hz, J'=2.5 Hz, 6$\beta$-CH); 3.67 (2H, s, SCH$_2$Ph); 3.74 (3H, s, CO$_2$CH$_3$); 4.67 (1H, br.t., J=8 Hz, =CH—CH$_2$); 5.05 (1H, br.s, 3-CH); 5.67 (1H, d, J=2.5 Hz, 5-CH); 7.29$\delta$ (5H, s, SCH$_2$Ph). $[\alpha]_D^{21}$=+26° (c=1.69 MeOH).

The approximate $\beta$-lactamase inhibition I$_{50}$ values in $\mu$g/ml for the title compound were as follows:

| Escherichia coli JT4 | 0.15 |
| Klebsiella aerogenes E70 | 0.28 |
| Staphylococcus aureus Russell | 0.01 |
| Proteus mirabilis C889 | 0.52 |
| Pseudomonas aeruginosa A | 0.54 |
| Pseudomonas dalgleish | 0.03 |
| Enterobacter P99 | 0.34 |

EXAMPLE 5

Methyl 3-(2-benzylsulphinylethylidene)-7-oxo-4-oxa-1-azabicyclo[3,2,0]heptane-2-carboxylate and methyl 3-(2-benzylsulphonylethylidene)-7-oxo-4-oxa-1-azabicyclo[3,2,0]heptane-2-carboxylate

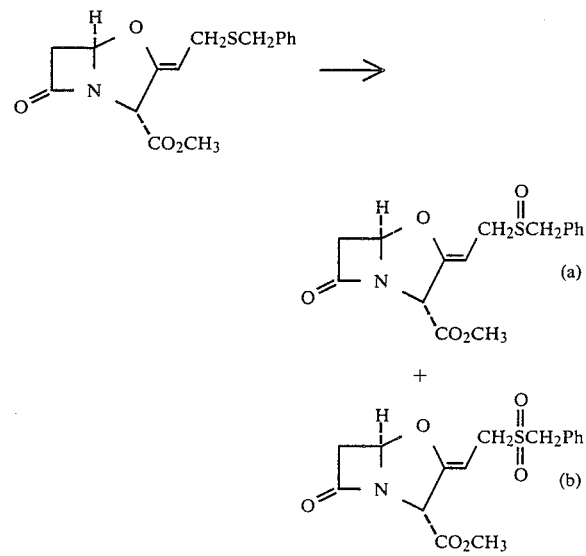

Methyl 3-(2-thiobenzylethylidene)-7-oxo-4-oxa-1-azabicyclo[3,2,0]heptane-2-carboxylate (95 mg) was dissolved in dry methylene dichloride (5 ml) and treated with m-chloroperbenzoic acid (78 mg) at 0° C. The solution stirred at 0° C. for half an hour and washed with 3% sodium bicarbonate solution (3×5 ml). The organic phase was dried over magnesium sulphate and the solvent evaporated to yield after chromatography as the first eluted product methyl 3-(2-benzylsulphonylethylidene)-7-oxo-4-oxa-1-azabicyclo[3,2,0]heptane-2-carboxylate (b) as a colourless oil (28 mg; 27%).

I.r. (CHCl$_3$): 1805, 1755, 1695 cm$^{-1}$.

N.m.r. (CDCl$_3$): 3.02 (1H, d, J=17 Hz, 6$\beta$-CH); 3.50 (1H, dd, J=17 Hz, J'=2.5 Hz, 6$\alpha$-CH); 3.65 (2H, d, J=8 Hz, =CH—e,uns/CH/ $_2$); 3.75 (3H, s, CO$_2$CH$_3$); 4.13 (2H, s, CH$_2$Ph); 4.74 (1H, br.t, J=Hz, =CH—CH$_2$); 5.14 (1H, br.s, 3-CH); 5.75 (1H, d, J=2.5 Hz, 5-CH); 7.37$\delta$ (5H, s, CH$_2$Ph).

$[\alpha]_D^{21}$=+8.2° (c=1.15, MeOH).

The approximate $\beta$-lactamase inhibition I$_{50}$ values in $\mu$g/ml for (b) were as follows:

| Escherichia coli JT4 | <0.0076 |
| Klebsiella aerogenes E70 | 0.12 |
| Staphylococcus aureus Russell | 0.01 |
| Proteus mirabilis C889 | 0.16 |
| Pseudomonas aeruginosa A | 0.025 |
| Pseudomonas dalgleish | <0.0076 |
| Enterobacter P99 | 0.015 |

The second product (a) to be eluted from the column was collected as a colourless oil I.r. (CHCl$_3$): 1800, 1755, 1690 cm$^{-1}$.

N.m.r. (CDCl$_3$): 3.00 (1H, d, J=17 Hz, 6$\beta$-CH); 3.41 (2H, d, J=8 Hz, =CH—CH$_2$); 3.49 (1H, dd, J=17 Hz, J'=2.5 Hz, 6$\alpha$-CH); 3.75 (3H, s, CO$_2$CH$_3$); 3.90 (2H, s, CH$_2$Ph); 4.78 (1H, br.t, J=8 Hz, =CH—CH$_2$); 5.18

(1H, br.s, 3-CH); 5.73 (1H, d, J=2.5 Hz, 5-CH); 7.32δ (5H,s, CH2Ph). [α]$_D^{21}$=0° (c=0.78; MeOH).

The approximate β-lactamase inhibition I$_{50}$ values in μg/ml for (a) were as follows:

| Escherichia coli JT4 | 0.05 |
|---|---|
| Klebsiella aerogenes E70 | 0.86 |
| Staphylococcus aureus Russell | 0.12 |
| Proteus mirabilis C889 | 0.56 |
| Pseudomonas aeruginosa A | 0.10 |
| Pseudomonas dalgleish | 0.03 |
| Enterobacter P99 | <<0.076 |

EXAMPLE 6

Sodium 3-(2-thiobenzylethylidene)-7-oxo-4-oxa-1-azabicyclo[3,2,0]heptane-2-carboxylate

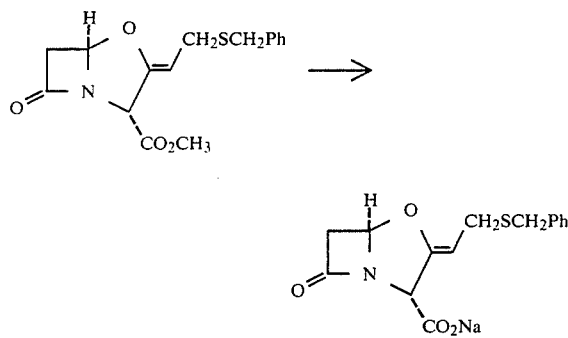

Methyl 3-(2-thiobenzylethylidene)-7-oxo-4-oxa-1-azabicyclo[3,2,0]heptane-2-carboxylate (95.7 mg) was hydrolysed using N NaOH at pH 9.5 (pH stat) until hydrolysis was complete. Chromatography (n-ButOH-/EtOH/H2O, 4/1/1) yielded the sodium salt as an amorphous solid after trituration with ether (32 mg; 31%).

I.r. (KBr): 1785, 1685 cm$^{-1}$.

N.m.r. (D2O): 3.05 (1H, d, J=17 Hz, 6β-CH); 3.15 (2H, d, J=8 Hz, =CH—CH2); 3.60 (1H, dd, J=17 Hz, J'=2.5 Hz, 6α-CH); 3.80 (2H, s, CH2Ph); 4.78 (=CH—CH2 proton partially obscured by D2O peak); 4.93 (1H, br.s, 3-CH); 5.70 (1H, d, J=2.5 Hz, 5-CH); 7.38δ (5H, s, CH2Ph). [α]$_D^{25}$=+19.8° (c=0.47; MeOH).

The approximate β-lactamase inhibition I$_{50}$ values in μg/ml for the title compound were as follows:

| Escherichia coli JT4 | 0.10 |
|---|---|
| Klebsiella aerogenes E70 | 0.13 |
| Staphylococcus aureus Russell | <0.0076 |
| Proteus mirabilis C889 | 0.016 |
| Pseudomonas aeruginosa A | >>4.0 |
| Pseudomonas dalgleish | 0.03 |
| Enterobacter P99 | >>4.0 |

EXAMPLE 7

Methyl 3-(2-thiophenylethylidene)-7-oxo-4-oxa-1-azabicyclo[3,2,0]heptane-2-carboxylate

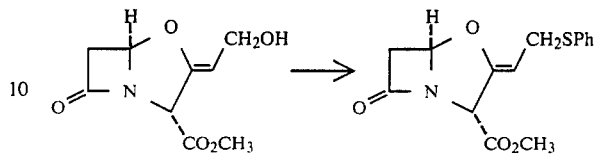

Methyl clavulanate (1 g) was dissolved in dry methylene dichloride (50 ml) and cooled to −30° C. Borontrifluoride etherate (15 drops; 0.18 ml) was added at −30° C. followed by a solution of thiophenol (550 mg) in methylene dichloride (10 ml). The mixture was stirred at −30° C. to −10° C. for two hours and washed with 3% sodium bicarbonate solution (3×50 ml). The organic phase was dried over magnesium sulphate and the solvent evaporated to yield an oil which after chromatography gave the title compound as a colourless oil (298 mg; 20%).

I.r. (CHCl3): 1800, 1755, 1695 cm$^{-1}$.

N.m.r. (CDCl3): 2.76 (1H, J=17 Hz, 6β-CH); 3.38 (1H, dd, J=17 Hz, J'=2.5 Hz, 6α-CH); 3.56 (2H, d, J=8 Hz, =CH—CH2); 3.64 (3H, s, CO2CH3); 4.70 (1H, br.t, J=8 Hz, =CH—CH2); 4.97 (1H, br.s, 3-CH); 5.60 (1H, d, J=2.5 Hz, 5-CH); 7.32δ (5H, br.s, SPh). [α]$_D^{20}$=+2° (c=1.16; MeOH).

The approximate β-lactamase inhibition I$_{50}$ values in μg/ml for the title compound were as follows:

| Escherichia coli JT4 | 0.01 |
|---|---|
| Klebsiella aerogenes E70 | 1.1 |
| Staphylococcus aureus Russell | 0.04 |
| Proteus mirabilis C889 | 1.72 |
| Pseudomonas aeruginosa A | 0.08 |

EXAMPLE 8

Benzyl 3-(2-thio-5-methoxythiadiazolylethylidene)-7-oxo-4-oxa-1-azabicyclo[3,2,0]heptane-2-carboxylate

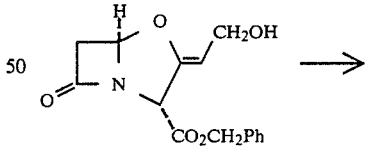

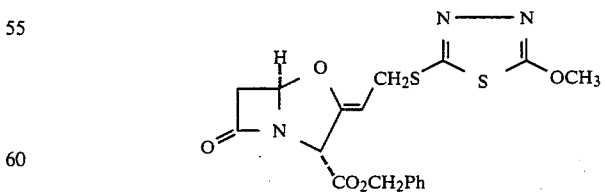

Benzyl clavulanate (2.89 g) was dissolved in dry methylene dichloride (100 ml) and treated with boron trifluoride etherate (50 drops; 0.6 ml) at −30° C. A solution of 5-methoxythiadiazolyl-2-thiol (1.48 g) in methylene dichloride (10 ml) was added dropwise over half an hour at −30° C. The reaction was stirred at −30° to −10° C. for two hours and worked up as described for the previous example. The title product was collected as a colourless oil (625 mg; 15%).

I.r. (CHCl$_3$): 1800, 1750, 1695 cm$^{-1}$.

N.m.r. (CDCl$_3$): 2.92 (1H, d, J=17 Hz, 6β-C$\underline{H}$); 3.40 (1H, dd, J=17 Hz, J'=2.5 Hz, 6α-C$\underline{H}$); 3.76 (2H, d, J=8 Hz, =CH—C$\underline{H_2}$); 4.03 (3H, s, OC$\underline{H_3}$); 5.02 (2H, br.s,=C$\underline{H}$—CH$_2$ and 3-C$\underline{H}$); 5.17 (2H, s, CO$_2$C$\underline{H_2}$Ph); 5.69 (1H, d, J=2.5 Hz, 5-C$\underline{H}$); 7.35δ (5H, s, CO$_2$CH$_2$P$\underline{h}$). [α]$_D^{23}$ = +5° (c=0.92; MeOH).

EXAMPLE 9

Methyl 3-[2-thio(ethoxycarbonylmethyl)ethylidene]-7-oxo-4-oxa-1-azabicyclo[3,2,0]heptane-2-carboxylate

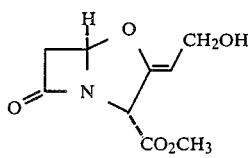

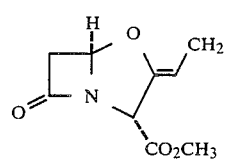

The title compound was prepared from methyl clavulanate by a process analogous to that described in Example 7 but in which the thiophenol was replaced by an equivalent amount of ethyl 1-mercaptoacetate.

EXAMPLE 10

Sodium 3-[2-thio(ethoxycarbonylmethyl)ethylidene]-7-oxo-4-oxa-1-azabicyclo[3,2,0]heptane-2-carboxylate

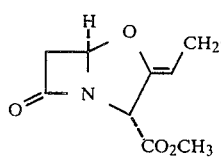

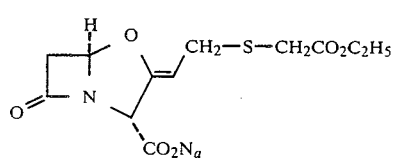

The title compound was prepared from the corresponding methyl ester by hydrolysis using N NaOH at pH 9–9.5 (pH stat) until one equivalent of base was consumed. Chromatography yielded the sodium salt as an amorphous solid after trituration with ether.

EXAMPLE 11

Benzyl 3-(2-thioethyl)ethylidene-7-oxo-4-oxa-1-azabicyclo[3,2,0]heptane-2-carboxylate

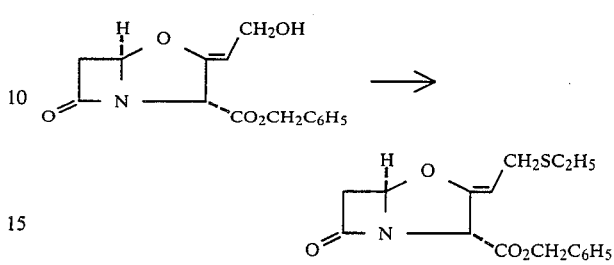

Benzyl clavulanate (3.18 g) was dissolved in methylene chloride (100 ml) and cooled to −30° C. A solution of ethyl mercaptan (1.0 ml) in methylene chloride (5 ml) was added, followed by boron trifluoride etherate (20 drops). The solution was stirred at −20° C. to −10° C. for 2.5 hours, washed with dilute sodium bicarbonate solution (×3) and the extract dried over MgSO$_4$. Evaporation of the solvent and chromatography yielded the title compound (804 mg) as a colourless oil;

I.r. (CHCl$_3$) 1800, 1750, 1695 cm$^{-1}$;

N.m.r. (CDCl$_3$) 1.22 (3H, t, J 6 Hz, —CH$_2$—C$\underline{H_3}$), 2.40 (2H, q, J 6 Hz, —C$\underline{H_2}$—CH$_3$), 2.95 (1H, d, J 17 Hz, 6β-C$\underline{H}$), 3.42 (1H, d, J 17 Hz, J' 2.5 Hz, 6α-C$\underline{H}$), 3.17 (2H, d, J 8 Hz, C$\underline{H_2}$SC$_2$H$_5$), 4.60 (1H, t, J 8 Hz, =CH—C$\underline{H_2}$—), 5.00 (1H, br s, 3-C$\underline{H}$), 5.18 (2H, s, CO$_2$C$\underline{H_2}$Ph), 5.73 (1H, d, J 2.5 Hz, 5-C$\underline{H}$), 7.36 (5H, s, CO$_2$CH$_2$P$\underline{h}$); [α]$_D^{20}$ = +13.1° (c=0.88; MeOH); M.w (Mass spectrometry) C$_{17}$H$_{19}$NO$_4$S: 333.103710 (expt.), 333.103469 (calc.).

EXAMPLE 12

Benzyl 3-(2-ethylsulphinylethylidene)-7-oxo-4-oxa-1-azabicyclo[3,2,0]heptane-2-carboxylate

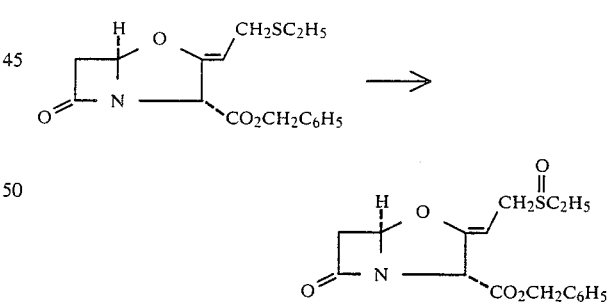

Benzyl 3-(2-ethylthioethylidene)-7-oxo-4-oxa-1-azabicyclo[3,2,0]heptane-2-carboxylate (704 mg) was dissolved in methylene chloride (40 ml) and treated with m-chloroperbenzoic acid (370 mg). The solution was stirred at 0° C. for 1.0 hour and washed with a dilute bicarbonate solution (×2). The extract was dried over MgSO$_4$ and evaporated. Chromatography over silica gel yielded the title product as a mixture of R and S sulphoxides (295 mg);

Ir. (CHCl$_3$) 1805, 1750, 1695 cm$^{-1}$; N.m.r. (CDCl$_3$) 1.18 (3H, t, J 6 Hz, —CH$_2$—C$\underline{H_3}$), 2.46 (2H, q, J 6 Hz, —C$\underline{H_2}$—CH$_3$), 2.90 (1H, d, J 17 Hz, 6β-C$\underline{H}$), 3.40 (1H, d, J 17 Hz, J' 2.5 Hz, 6α-C$\underline{H}$), 3.34

(2H, d, J 7Hz, CH$_2$SC$_2$H$_5$),

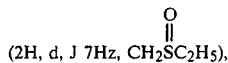

(1H, t, J 7 Hz, =CH—CH$_2$), 5.03 (3H, br s, 3-CH and CO$_2$CH$_2$Ph), 5.72 (1H, d, J 2.5 Hz, 5-CH), 7.30 (5H, s, CO$_2$CH$_2$Ph). M.w. (mass spectrometry) 349.

EXAMPLE 13

Allyl 3-[2-(β-hydroxyethyl)-thioethylidene]-7-oxo-4-oxa-1-azabicyclo[3,2,0]heptane-2-carboxylate

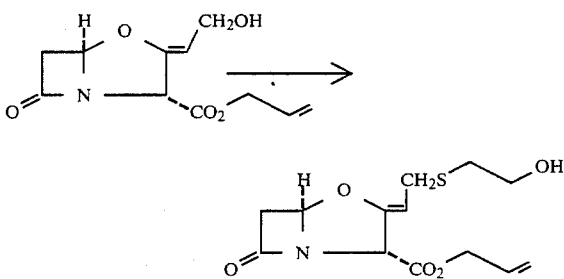

Allyl clavulanate (500 mg) was dissolved in methylene chloride (20 ml) and treated with 2-mercaptoethanol (0.25 ml) and boron trifluoride diethyletherate (25 drops). The solution was stirred at −20° to −10° C. for a period of 1.5 hours. The reaction was quenched with dilute sodium hydroxide solution and the organic extract washed with water and dried over MgSO$_4$. Evaporation of the solvent and column chromatography isolated the title compound (22 mg) as a colourless oil;

I.r. (CHCl$_3$) 3450-3550, 1805, 1750, 1695 cm$^{-1}$;

N.m.r. (CDCl$_3$) 2.62 (2H, t, J 6 Hz, S—CH$_2$—CH$_2$), 3.00 (1H, d, J 17 Hz, 6β-CH), 3.17 (2H, d, J 8 Hz, =CH—CH$_2$S), 3.44 (1H, dd, J 17 Hz, J' 2.5 Hz, 6α-CH), 3.64 (2H, t, J 6 Hz, CH$_2$—CH$_2$OH), 4.62 (2H, d, J 6 Hz, CO$_2$CH$_2$), 4.68 (1H, t J 8 Hz, =CH—CH$_2$S), 5.02 (1H, br.s, 3-CH), 5.30 (2H, m, =CH$_2$), 5.63 (1H, d, J 2.5 Hz, 5-CH), 5.7-6.1 (1H, m, CH$_2$—CH=CH$_2$).

EXAMPLE 14

Benzyl 3-[2-(β-ethoxycarbonyl)methylthio]ethylidene-7-oxo-4-oxa-1-azabicyclo[3,2,0]heptane-2-carboxylate

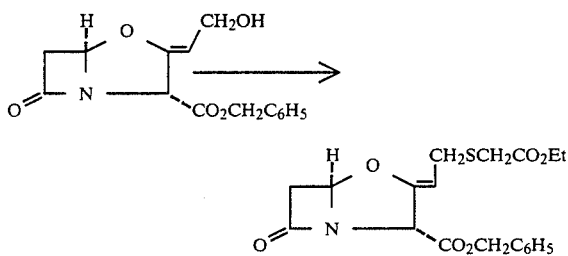

Benzyl clavulanate (1.9 g) and ethyl 2-mercaptoacetate (1.5 g) were dissolved in methylene chloride and stirred at −20° C. Boron trifluoride diethyletherate (0.2 ml) was added and the solution stirred at −20° C. to −10° C. for 2.0 hours. The reaction was quenched with a 3% solution of sodium bicarbonate. The organic extract was washed with bicarbonate solution, sodium chloride solution, and then dried over MgSO$_4$. The product (95 mg) was isolated as a colourless oil, after chromatography over silica gel (eluting ethyl acetate/cyclohexane);

I.r. (CHCl$_3$) 1800, 1735-1750, 1695 cm$^{-1}$; N.m.r. (CDCl$_3$) 1.28 (3H, t, J 7 Hz, CH$_2$CH$_3$), 3.12 (2H, s, SCH$_2$CO$_2$Et), 3.10 (1H, d, J 17 Hz, 6β-CH), 3.36 (2H, d, J 8 Hz, =CH—CH$_2$), 3.55 (1H, d, J 17 Hz, J' 2 Hz, 6α-CH), 4.23 (2H, q, J 7 Hz, CH$_2$CH$_3$), 4.83 (1H, t, J 8 Hz, =CH—CH$_2$), 5.18 (1H, s, 3-CH), 5.28 (2H, s, CO$_2$CH$_2$Ph), 5.76 (1H, d, J 2 Hz, 5-CH), 7.42 (5H, s, CO$_2$CH$_2$Ph).

EXAMPLE 15

Methoxymethyl-3-(2-thioethyl)ethylidene-7-oxo-4-oxa-1-azabicyclo[3,2,0]heptane-2-carboxylate

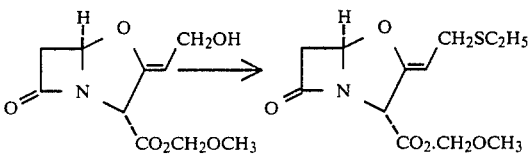

Methoxymethyl clavulanate (1.0 g) was dissolved in methylene chloride (25 ml) and cooled to −30° C. Ethyl mercaptan (0.5 ml) was added, followed by boron trifluoride etherate (0.2 ml). The solution was stirred at −20° C. to −10° C. for 2.0 hours, washed with dilute sodium bicarbonate solution (×2), and brine (×2), and the extract dried over MgSO$_4$. Evaporation of the solvent and chromatography yielded the title compound (101 mgs) as a colourless oil;

N.m.r. (CDCl$_3$) 1.37 (3H, t, J 7 Hz, S—CH$_2$—CH$_3$) 2.60 (2H, q, J 7 Hz, S—CH$_2$—CH$_3$), 3.13 (1H, d, J 17 Hz, 6β-CH), 3.41 (2H, d, J 8 Hz, =CH—CH$_2$S), 3.65 (1H, dd, J 17 Hz, J' 2.5 Hz, 6α-CH), 3.64 (3H, s, —OCH$_3$), 4.94 (1H, t, J 8 Hz, =CH—CH$_2$), 5.27 (1H, br.s, 3-CH), 5.85 (1H, d, J 2.5 Hz, 5-CH), 5.48 (2H, q, J 4 Hz, CO$_2$CH$_2$OCH$_3$).

[Methoxymethyl clavulanate may be prepared by the reaction of sodium clavulanate with chloromethyl methyl ether in dimethylformamide].

EXAMPLE 16

Methyl 3-(2-thioethyl)ethylidene-7-oxo-4-oxa-1-azabicyclo[3,2,0]heptane-2-carboxylate

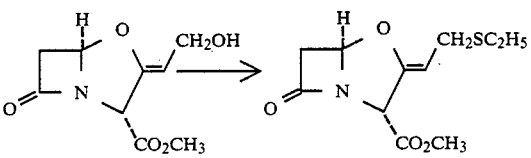

Methyl clavulanate (3.0 g) was dissolved in methylene chloride, and ethyl mercaptan (0.9 ml) added, followed by boron trifluoride etherate (1.0 ml). The solution was stirred at room temperature for 3.0 hours, quenched with sodium bicarbonate solution, and the organic extract washed with brine. Evaporation of the solvent and chromatography yielded the title compound (78 mgs) as a clear oil; νmax (CHCl$_3$) 1800, 1750, 1690 cm$^{-1}$; N.m.r. (CDCl$_3$) 1.27 (3H, t, J 7 Hz, S—CH$_2$—CH$_3$), 2.74 (2H, q, J 7 Hz, S—CH$_2$—CH$_3$), 3.07 (1H, d, J 17 Hz, 6β-CH), 3.30 (2H, d, J 7 Hz, =CH—CH$_2$), 3.70 (1H, dd, J 17 Hz, J' 2.5 Hz, 6α-CH), 3.86 (3H, s, —CO$_2$CH$_3$), 4.84 (1H, t, J 7 Hz, =CH—CH$_2$), 5.17 (1H, s, 3-CH), 5.77 (1H, d, J 2.5 Hz, 5-CH).

EXAMPLE 17

Sodium 3-(2-thioethyl)ethylidene-7-oxo-4-oxa-1-azabicyclo[3,2,0]heptane-2-carboxylate

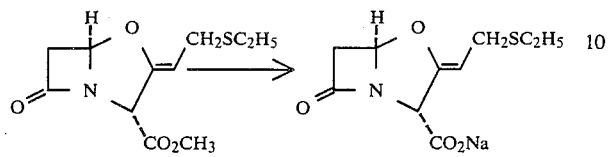

The methyl ester (70 mgs) was dissolved in tetrahydrofuran (10 ml) and water (30 ml). Hydrolysis of the thioether using N NaOH at constant pH (9.0) provided the sodium salt in good yield (50 mgs); νmax (KBr) 1785, 1690, 1600 cm$^{-1}$; N.m.r. (D$_2$O) 1.05 (3H, t, J 7 Hz, SCH$_2$—CH$_3$), 2.37 (2H, q, J 7 Hz, SCH$_2$CH$_3$), 2.90 (1H, d, J 17 Hz, 6β-CH), 3.14 (2H, d, J 7 Hz, =CH—CH$_2$), 3.40 (1H, dd, J 17 Hz, J' 2.5 Hz, 6α-CH), 4.65 (1H, t, J 7 Hz, =CH—CH$_2$), 4.79 (1H, s, 3-CH), 5.58 (1H, d, J 2.5 Hz, 5-CH).

EXAMPLE 18

Anthrylmethyl 3-(2-thioethyl)ethylidene-7-oxo-4-oxa-1-azabicyclo[3,2,0]heptane-2-carboxylate

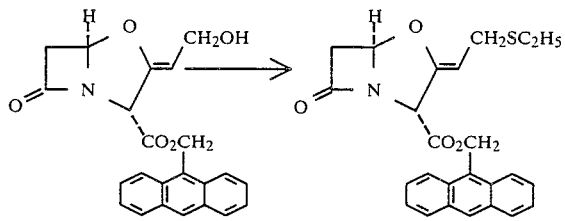

Anthrylmethyl clavulanate (1.3 g) was dissolved in methylene chloride, and the solution at −70° C. treated with ethyl mercaptan (0.2 ml) and boron trifluoride etherate (20 drops). The reaction mixture was allowed to warm up to −30° C. with stirring and then quenched with sodium bicarbonate solution. The organic extract was washed with brine (×2) and dried over MgSO$_4$. Chromatography isolated the product as a yellow oil (207 mgs);

νmax (CHCl$_3$) 1800, 1750, 1695 cm$^{-1}$; n.m.r. (CDCl$_3$) 1.13 (3H, t, J 7 Hz, S—CH$_2$CH$_3$), 2.28 (2H, q, J 7 Hz, S—CH$_2$—CH$_3$), 2.95 (1H, d, J 17 Hz, 6β-CH), 3.10 (2H, d, J 7 Hz, =CH—CH$_2$), 3.40 (1H, dd, J 17 Hz, J' 2.5 Hz, 6α-CH) 4.54 (1H, t, J 7 Hz, =CH—CH$_2$), 5.05 (1H, s, 3-CH), 5.55 (1H, d, J 2.5 Hz, 5-CH), 6.16 (2H, s, —CO$_2$CH$_2$), 7.2–8.5 (9H, m, aryl). The starting material for the preceding example may be produced thus:

Sodium clavulanate (0.5 g) and 9-chloromethylanthracene (1.0 g) were stirred in dimethylformamide overnight at room temperature. After evaporation of the solvent, the residue was taken up in ethyl acetate and water. The organic layer was washed with brine, dried over MgSO$_4$ and evaporated. Chromatography isolated the product (0.5 g) as a yellow crystalline solid, m pt. 120° C., νmax 1800, 1740, 1698 cm$^{-1}$;

N.m.r. (CDCl$_3$) 1.36 (1H, br.s, —OH), 2.90 (1H, d, J 17 Hz, 6β-CH), 3.35 (1H, dd, J 17 Hz, J' 2.5 Hz, 6α-CH), 3.98 (2H, d, J 7 Hz, =CH—CH$_2$), 4.62 (1H, t, J Hz, =CH—CH$_2$), 4.80 (1H, s, 3-CH), 5.52 (1H, d, J 2.5 Hz, 5-CH), 6.14 (2H, s, CO$_2$CH$_2$), 7.16–8.42 (9H, m, aryl).

EXAMPLE 19

Methoxymethyl 3-(2-thiomethyl)ethylidene-7-oxo-4-oxa-1-azabicyclo[3,2,0]heptane-2-carboxylate

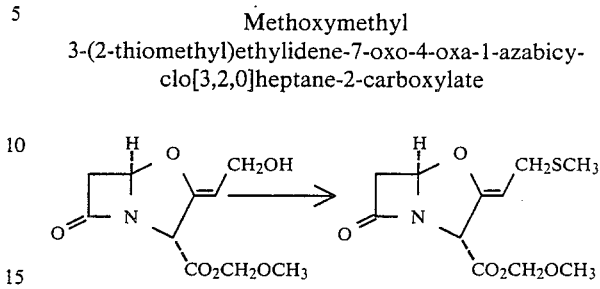

Methoxymethyl clavulanate (2.3 g) was dissolved in methylene chloride (50 ml). The stirring solution was cooled to −30° C. and boron trifluoride etherate (0.5 ml) added. Methyl mercaptan was bubbled, at a slow rate, through the solution for 1.0 hour, the temperature being held at −20° C. to −10° C. The solution was then stirred at −10° C. for a further 0.5 hours. Nitrogen gas was then bubbled through the solution and the reaction subsequently quenched with a 3% solution of sodium bicarbonate. The organic extract was washed with bicarbonate, brine (×2), and dried over sodium sulphate. The solution was filtered and evaporated. Column chromatography over silica gel [eluting ethyl acetate/petrol (60–80)] yielded the title compound as a clear oil. Yield 185 mgs; νmax (CHCl$_3$) 1795–1810, 1755, and 1695 cm$^{-1}$;

N.m.r. (CDCl$_3$) 1.96 (3H, s, S—CH$_3$), 2.98 (1H, d, J17 Hz, 6β—CH), 3.17 (2H, d, J 7 Hz, =CH—CH$_2$S), 3.50 (1H, dd, J 17 Hz, J' 2.5 Hz, 6α-CH), 3.45 (3H, s, —OCH$_3$), 4.77 (1H, t, J 7 Hz, =CH—CH$_2$), 5.10 (1H, br.s 3-CH), 5.32 (2H, m, CO$_2$CH$_2$), 5.72 (1H, d, J 2.5 Hz, 5-CH).

EXAMPLE 20

Lithium 3-(2-thiomethyl)ethylidene-7-oxo-4-oxa-1-azabicyclo[3,2,0]heptane-2-carboxylate

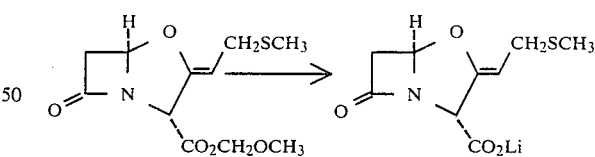

The methoxymethyl ester (130 mgs) was dissolved in tetrahydrofuran (10 ml) and water (40 mls) and the solution subjected to hydrolysis with N lithium hydroxide at a constant pH of 9 for 30 minutes. The volume of the solution was reduced to 5 ml by evaporation under reduced pressure and the residue thoroughly triturated with acetone (15 ml). The solid white product was filtered off and washed with ether.

Yield 98 mgs, νmax (KBr) 1760, 1690, 1610 cm$^{-1}$;

N.m.r. (D$_2$O) 1.87 (3H, s, S—CH$_3$), 2.86 (1H, d, J 17 Hz, 6β-CH), 3.03 (2H, d, J 7 Hz, =CH—CH$_2$), 3.38 (1H, dd, J 17 Hz, J' 2.5 Hz, 6α-CH), 4.61 (1H, t, J 7 Hz, =CH—CH$_2$), 4.77 (1H, s, 3-CH), 5.61 (1H, d, J 2.5 Hz, 5-CH).

EXAMPLE 21

Lithium 3-(2-thioethyl)ethylidene-7-oxo-4-oxa-1-azabicyclo[3,2,0]heptane-2-carboxylate

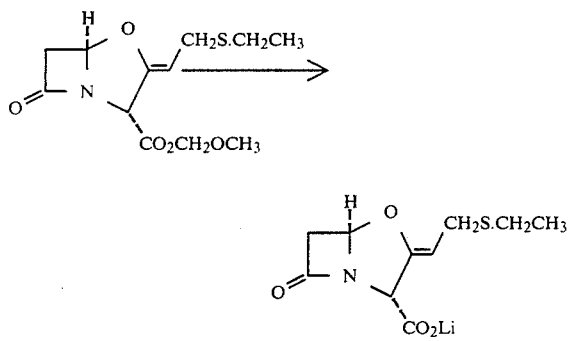

The methoxymethyl ester (70 mgs) was dissolved in tetrahydrofuran (10 ml) and water (30 ml) and the solution subjected to hydrolysis with N lithium hydroxide at a constant pH of 9 for 35 minutes. The solution was evaporated under reduced pressure and the residue thoroughly triturated with acetone (20 ml). The solid product was filtered off and washed with ether (2×10 ml).

Yield (30 mgs), $\nu$max (KBr) 1760, 1690, 1610 cm$^{-1}$;

N.m.r. (D$_2$O) 1.20 (3H, t, J 7 Hz, SCH$_2$—C$\underline{H}_3$), 2.50 (2H, q, $\underline{J}$ 7 Hz, SC$\underline{H}_2$CH$_3$), 3.05 (1H, d, $\underline{J}$ 17 Hz, 6$\beta$-CH), 3.27 (2H, d, $\underline{J}$ 7 Hz, =CH—C$\underline{H}_2$), 3.55 (1H, dd, $\underline{J}$ 17 Hz, J' 2.5 Hz, 6$\alpha$-C$\underline{H}$), 4.68 (1H, t, J 7 Hz, =C$\underline{H}$—CH$_2$), 4.92 (1H, s, 3-C$\underline{H}$), 5.70 (1H, d, $\underline{J}$ 2.5 Hz, 5-C$\underline{H}$).

EXAMPLE 22

Lithium 3-(2-methylsulphinyl)ethylidene-7-oxo-4-oxa-1-azabicyclo[3,2,0]heptane-2-carboxylate

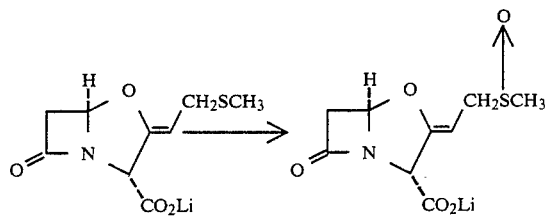

The thioether (60 mg) was dissolved in distilled water (10 ml) and treated with m-chloroperbenzoic acid (44 mg). The mixture was stirred at ice-temperature for 3 hours. The m-chlorobenzoic acid was filtered off. The solution was evaporated under reduced pressure, and the residue triturated with acetone (10 ml). The solid white product was collected and washed with dry ether. Yield 28 mg.

$\nu_{max}$ (KBr) 1785, 1690 and 1520 (broad) cm$^{-1}$.

EXAMPLE 23

Lithium 3-(2-ethylsulphinylethylidene)-7-oxo-4-oxa-1-azabicyclo[3,2,0]heptane-2-carboxylate

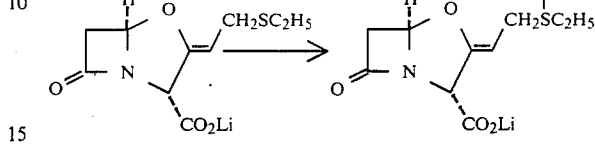

The thioether (25 mg) was dissolved in distilled water (4 ml) and treated with m-chloroperbenzoic acid (20 mg). The mixture was stirred at ice-temperature for 4 hours. The m-chlorobenzoic acid was filtered off. The solution was freeze-dried to give the sulphoxide salt as a white solid (20 mg).

$\nu_{max}$ (KBr) 1780, 1685, and 1630 (broad) cm$^{-1}$.

EXAMPLE 24

A. Sodium 3-(2-thiobenzylethylidene)-7-oxo-4-oxa-1-azabicyclo[3,2,0]heptane-2-carboxylate (50 mg) may be dissolved in sterile physiological saline (10 ml) to give a solution suitable for injection.

B. Sodium 3-(2-thioethylethylidene)-7-oxo-4-oxa-1-azabicyclo[3,2,0]heptane-2-carboxylate (50 mg) may be dissolved in sterile physiological saline (10 ml) and mixed with a solution of sodium amoxycillin (250 mg) in water for injection (5 ml) to give a solution suitable for immediate injection.

What we claim is:

1. A pharmaceutical composition for treating bacterial infections in humans and animals which comprises a synergistically effective amount of a compound of the formula (II):

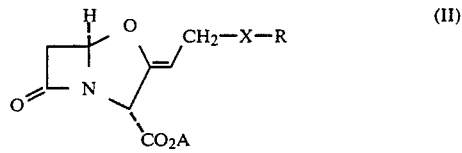

wherein X is S, SO or SO$_2$, R is an inert hydrocarbon of up to 20 carbon atoms unsubstituted or substituted by halogen, by a member selected from the group consisting of OR$^1$, O.COR$^1$, CO.R$^1$, CO$_2$R$^1$, NHR$^1$, NR$^1$R$^2$, NH.CO.R$^1$, NR$^2$CO$^1$, NHCO$_2$R$^1$ and NR$^2$CO$_2$R$^1$ wherein R$^1$ is hydrogen or a hydrocarbon of up to 8 carbon atoms and R$^2$ is alkyl of 1 to 3 carbon atoms, or by halogen and a member of said group which will not lead to rapid degradation of the compound of the formula (II), or R is a heteroaromatic ring of 5 or 6 ring members unsubstituted or substituted by alkyl of up to 3 carbon atoms or by alkyl of up to 3 carbon atoms substituted by CONH$_2$ or CO$_2$H and A is a group such that CO$_2$A represents a carboxylic acid group or a non-toxic salt or non-toxic ester thereof, and an antibacterially effective amount of a penicillin, in combination with a pharmaceutically acceptable carrier.

2. A composition according to claim 1 wherein R is an unsubstituted hydrocarbon of up to 20 carbon atoms.

3. A composition according to claim 1 wherein R is a hydrocarbon of up to 20 carbon atoms substituted by halogen, by a member selected from the group consisting of $OR^1$, $O.COR^1$, $CO.R^1$, $CO_2R^1$, $NHR^1$, $NR^1R^2$, $NH.CO.R^1$, $NR^2CO^1$, $NHCO_2R^1$ and $NR^2CO_2R^1$ wherein $R^1$ is hydrogen or a hydrocarbon of up to 8 carbon atoms and $R^2$ is alkyl of 1 to 3 carbon atoms, or by halogen and a member of said group.

4. A composition according to claim 1 wherein R is alkyl of up to 6 carbon atoms.

5. A composition according to claim 1 wherein R is $CH_2R^3$ wherein $R^3$ is hydrogen, alkyl of up to 5 carbon atoms, haphthyl, or phenyl unsubstituted or substituted by halogen, hydroxyl or amino, or a group of the formula $R^4$, $OR^4$ or $NR^4R^5$ wherein $R^4$ is alkyl or acyl of up to 3 carbon atoms and $R^5$ is hydrogen or alkyl of up to 4 carbon atoms.

6. A composition according to claim 1 wherein R is $CR^6R^7R^8$ wherein $R^6$ and $R^7$ are each alkyl of up to 3 carbon atoms or phenyl unsubstituted or substituted by halogen, $R^9$ or $OR^9$ wherein $R^9$ is alkyl of up to 3 carbon atoms and $R^8$ is hydrogen, alkyl of up to 3 carbon atoms or phenyl unsubstituted or substituted by halogen, $R^{10}$ or $OR^{10}$ is alkyl of up to 3 carbon atoms.

7. A composition according to claim 1 wherein R is $R^{11}$, wherein $R^{11}$ is a heteroaromatic ring of 5 or 6 ring members, unsubstituted or substituted by alkyl of up to 3 carbon atoms or alkyl of up to 3 carbon atoms substituted by $CONH_2$ or $CO_2H$.

8. A composition according to claim 1 wherein $R^{11}$ is triazole, tetrazole, thienyl, thiazole, thiadazole, thiatriazole, oxazole, isoxazolyl, oxadiazole, pyridyl, pyridazinyl or pyrimidinyl.

9. A composition according to claim 1 wherein R is phenyl unsubstituted or substituted by $OR^1$, $O.COR^1$, $COR^1$ or $CO_2R^1$, wherein $R^1$ is hydrogen or a hydrocarbon of up to 8 carbon atoms or by chloro, bromo or fluoro.

10. A composition according to claim 1 wherein the compound is of the formula (III):

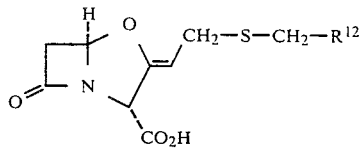

(III)

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$, wherein $R^{13}$ is a hydrocarbon of up to 8 carbon atoms.

11. A composition according to claim 1 wherein the compound is of the formula

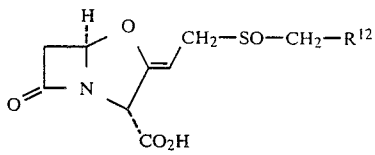

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$ wherein $R^{13}$ is a hydrocarbon of up to 8 carbon atoms.

12. A composition according to claim 1 wherein the compound is of the formula

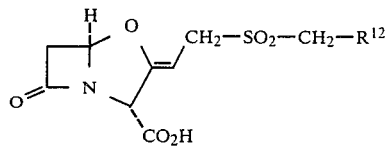

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$ wherein $R^{13}$ is a hydrocarbon of up to 8 carbon atoms.

13. A composition according to claim 1 wherein the compound is of the formula (IV):

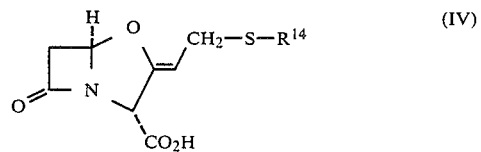

(IV)

or a pharmaceutically acceptable salt thereof wherein $R^{14}$ is a 5-membered heterocyclic ring substituted or unsubstituted by alkyl of up to 3 carbon atoms.

14. A composition according to claim 1 wherein the 5-membered heterocyclic ring of $R^{14}$ contains 3 or 4 heteroatoms, at least 2 of which are nitrogen atoms.

15. A composition according to claim 1 wherein $R^{14}$ is wherein $X^1—Y^1$ is $S—N(CH_3)$, $O—N(CH_3)$, $N—N(CH_3)$, $N—CH_2$, $O—CH_2$ or $S—CH_2$.

16. A composition according to claim 1 wherein the compound is of the formula (V):

(V)

or a pharmaceutically acceptable salt thereof wherein $R^{15}$ is a divalent hydrocarbon of 1–8 carbon atoms and $R^{16}$ is hydrogen or a hydrocarbon of 1–8 carbon atoms.

17. A composition according to claim 16 wherein $R^{15}$ is alkylene of 1 to 4 carbon atoms or alkyl of 1 or 2 carbon atoms substituted by phenyl.

18. A composition according to claim 16 wherein $R^{15}$ is hydrogen, alkylene of 1 to 4 carbon atoms or alkylene of 1 or 2 carbon atoms substituted by phenyl.

19. A composition according to claim 1 wherein the compound is of the formula (V):

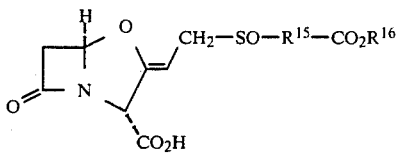

or a pharmaceutically acceptable salt thereof wherein $R^{15}$ is a divalent hydrocarbon of 1-8 carbon atoms and $R^{16}$ is hydrogen or a hydrocarbon of 1-8 carbon atoms.

20. A composition according to claim 1 wherein the compound is of the formula (V):

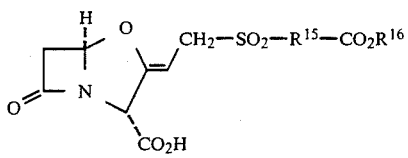

or a pharmaceutically acceptable salt thereof wherein $R^{15}$ is a divalent hydrocarbon of 1-8 carbon atoms and $R^{16}$ is hydrogen or a hydrocarbon of 1-8 carbon atoms.

21. A composition according to claim 1 wherein R is methyl, ethyl, n-propyl, n-butyl, 2-methoxyethyl, 2-benzyloxymethyl, 2-ethoxyethyl, 3-methoxypropyl, benzyl, p-chlorobenzyl, p-methoxybenzyl, m-methoxybenzyl, m-methylbenzyl, phenyl, 4-fluorophenyl or 2-phenylethyl.

22. A composition according to claim 1 wherein A is hydrogen or a sodium, potassium, calcium, magnesium, ammonium, alkylamine, dialkylamine, trialkylamine or pyrrolidine ion.

23. A composition according to claim 1 wherein A is a pharmaceutically acceptable alkali metal ion.

24. A composition according to claim 1 wherein A is a pharmaceutically acceptable alkaline earth metal ion.

25. A composition according to claim 1 wherein the compound is in the form of the sodium salt.

26. A composition according to claim 1 wherein the compound is in the form of the potassium salt.

27. A composition according to claim 1 wherein the compound is in the form of a pharmaceutically acceptable salt in crystalline form.

28. A composition according to claim 1 wherein the compound is in the form of an ester wherein the ester is of the formulae

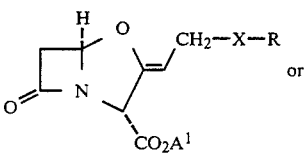

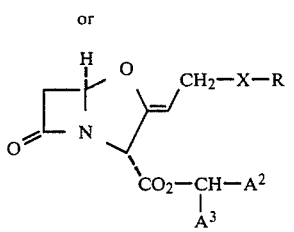

wherein X is S, SO or $SO_2$, R is an inert hydrocarbon of up to 20 carbon atoms unsubstituted or substituted by halogen, by a member selected from the group consisting of $OR^1$, $O.COR^1$, $CO.R^1$, $CO_2R^1$, $NHR^1$, $NR^1R^2$, $NH.CO.R^1$, $NR^2CO^1$, $NHCO_2R^1$ and $NR^2CO_2R^1$ wherein $R^1$ is hydrogen or a hydrocarbon of up to 8 carbon atoms and $R^2$ is alkyl of 1 to 3 carbon atoms, or by halogen and a member of said group which will not lead to rapid degradation of the compound of the formula (II), $A^1$ is alkyl of 1 to 8 carbon atoms unsubstituted or substituted by halogen, $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen, $A^5$ or $OA^5$ wherein $A^5$ is alkyl of up to 6 carbon atoms; and $A^3$ is phenyl unsubstituted or substituted by halogen, $A^5$ or $OA^5$ wherein $A^5$ is as above defined.

29. A composition according to claim 1 wherein the compound is in the form of the benzyl ester.

30. A composition according to claim 1 wherein the compound is in the form of the p-methoxybenzyl ester.

31. A composition according to claim 1 wherein the compound is in the form of a hydrogenalyzable ester.

32. A composition according to claim 1 wherein the compound of the formula (II) or its salt or ester thereof and said penicillin are present in a ratio of 1:10 to 3:1.

33. A composition according to claim 32 wherein the ratio is 1:5 to 2:1.

34. A composition according to claim 32 wherein the ratio is 1:1 to 2:1.

35. A composition according to claim 1 wherein the penicillin is benzylpenicillin.

36. A composition according to claim 1 wherein the penicillin is phenoxymethylpenicillin.

37. A composition according to claim 1 wherein the penicillin is carbenicillin.

38. A composition according to claim 1 wherein the penicillin is methicillin.

39. A composition according to claim 1 wherein the penicillin is propicillin.

40. A composition according to claim 1 wherein the penicillin is ampicillin.

41. A composition according to claim 1 wherein the penicillin is ticarcillin.

42. A composition according to claim 1 wherein the penicillin is cyclacillin.

43. A composition according to claim 1 wherein the penicillin is epicillin.

44. A composition according to claim 1 in oral administration form.

45. A composition according to claim 1 in parenteral administration form.

46. A composition according to claim 1 in injection administration form.

47. A composition according to claim 1 in a form suitable for administration by infusion.

48. A composition according to claim 1 wherein the penicillin is amoxycillin.

49. A composition according to claim 48 wherein the amoxycillin is in the form of a pharmaceutically acceptable salt, a hydrate or an in-vivo hydrolyzable ester.

50. A method of treating bacterial infections in humans and animals which comprises administering to a human or animal in need thereof a synergistically effective amount of a compound of the formula (II):

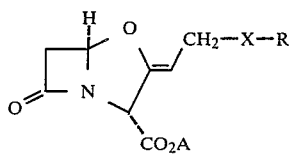

wherein X is S, SO or $SO_2$, R is an inert hydrocarbon of up to 20 carbon atoms unsubstituted or substituted by halogen, by a member selected from the group consisting of $OR^1$, $O.COR^1$, $CO.R^1$, $CO_2R^1$, $NHR^1$, $NR^1R^2$, $NH.CO.R^1$, $NR^2CO^1$, $NHCO_2R^1$ and $NR^2CO_2R^1$ wherein $R^1$ is hydrogen or a hydrocarbon of up to 8 carbon atoms and $R^2$ is alkyl of 1 to 3 carbon atoms, or by halogen and a member of said group which will not lead to rapid degradation of the compound of the formula (II), or R is a heteroaromatic ring of 5 or 6 ring members unsubstituted or substituted by alkyl of up to 3 carbon atoms or by alkyl of up to 3 carbon atoms substituted by $CONH_2$ or $CO_2H$ and A is a group such that $CO_2A$ represents a carboxylic acid group or a non-toxic salt or non-toxic ester thereof, and an antibacterially effective amount of a penicillin, in combination with a pharmaceutically acceptable carrier.

51. A method according to claim 50 wherein R is an unsubstituted hydrocarbon of up to 20 carbon atoms.

52. A method according to claim 50 wherein R is a hydrocarbon of up to 20 carbon atoms substituted by halogen, by a member selected from the group consisting of $OR^1$, $O.COR^1$, $CO.R^1$, $CO_2R^1$, $NHR^1$, $NR^1R^2$, $NH.CO.R^1$, $NR^2CO^1$, $NHCO_2R^1$ and $NR^2CO_2R^1$ wherein $R^1$ is hydrogen or a hydrocarbon of up to 8 carbon atoms and $R^2$ is alkyl of 1 to 3 carbon atoms, or by halogen and a member of said group.

53. A method according to claim 50 wherein R is alkyl of up to 6 carbon atoms.

54. A method according to claim 50 wherein R is $CH_2R^3$ wherein $R^3$ is hydrogen, alkyl of up to 5 carbon atoms, haphthyl, or phenyl unsubstituted or substituted by halogen, hydroxyl or amino, or a group of the formula $R^4$, $OR^4$ or $NR^4R^5$ wherein $R^4$ is alkyl or acyl of up to 3 carbon atoms and $R^5$ is hydrogen or alkyl of up to 4 carbon atoms.

55. A method according to claim 50 wherein R is $CR^6R^7R^8$ wherein $R^6$ and $R^7$ are each alkyl of up to 3 carbon atoms or phenyl unsubstituted or substituted by halogen, $R^9$ or $OR^9$ wherein $R^9$ is alkyl of up to 3 carbon atoms and $R^8$ is hydrogen, alkyl of up to 3 carbon atoms or phenyl unsubstituted or substituted by halogen, $R^{10}$ or $OR^{10}$ wherein $R^{10}$ is alkyl of up to 3 carbon atoms.

56. A method according to claim 50 wherein R is $R^{11}$, wherein $R^{11}$ is a heteroaramatic ring of 5 to 6 ring members, unsubstituted or substituted by alkyl of up to 3 carbon atoms or alkyl of up to 3 carbon atoms substituted by $CONH_2$ or $CO_2H$.

57. A method according to claim 50 wherein $R^{11}$ is triazole, tetrazole, thienyl, thiazole, thiadazole, thiatriazole, oxazole, isoxazolyl, oxadiazole, pyridyl, pyridazinyl or pyrimidinyl.

58. A method according to claim 50 wherein R is phenyl unsubstituted or substituted by $OR^1$, $O.COR^1$, $COR^1$ or $CO_2R^1$, wherein $R^1$ is hydrogen or a hydrocarbon of up to 8 carbon atoms or by chloro, bromo or fluoro.

59. A method according to claim 50 wherein the compound is of the formula (III):

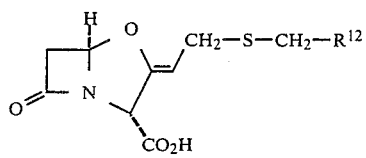

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$, wherein $R^{13}$ is a hydrocarbon of up to 8 carbon atoms.

60. A method according to claim 50 wherein the compound is of the formula

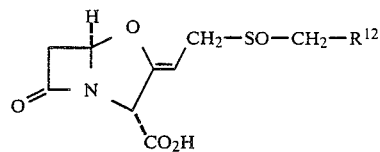

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$ wherein $R^{13}$ is a hydrocarbon of up to 8 carbon atoms.

61. A method according to claim 50 wherein the compound is of the formula

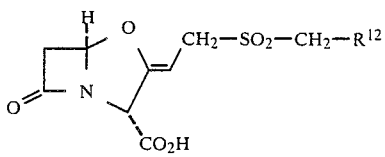

or a pharmaceutically acceptable salt thereof wherein $R^{12}$ is phenyl unsubstituted or substituted by chloro, fluoro, bromo, $OR^{13}$, $O.COR^{13}$, $COR^{13}$ or $CO_2R^{13}$ wherein $R^{13}$ is a hydrocarbon of up to 8 carbon atoms.

62. A method according to claim 50 wherein the compound is of the formula (IV):

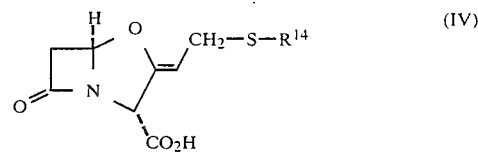

or a pharmaceutically acceptable salt thereof wherein $R^{14}$ is a 5-membered heterocyclic ring substituted or unsubstituted by alkyl of up to 3 carbon atoms.

63. A method according to claim 62 wherein the 5-membered heterocyclic ring of $R^{14}$ contains 3 or 4 heteroatoms, at least 2 of which are nitrogen atoms.

64. A method according to claim 62 wherein $R^{14}$ is

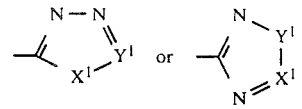

wherein $X^1$—$Y^1$ is $S-N(CH_3)$, $O-N(CH_3)$, $N-N(CH_3)$, $N-CH_2$, $O-CH_2$ or $S-CH_2$.

65. A method according to claim 50 wherein the compound is of the formula (V):

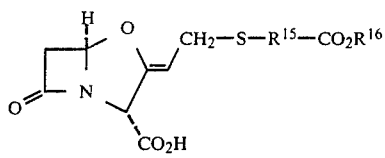 (V)

or a pharmaceutically acceptable salt thereof wherein $R^{15}$ is a divalent hydrocarbon of 1–8 carbon atoms and $R^{16}$ is hydrogen or a hydrocarbon of 1–8 carbon atoms.

66. A method according to claim 65 wherein $R^{15}$ is alkylene of 1 to 4 carbon atoms or alkyl of 1 or 2 carbon atoms substituted by phenyl.

67. A method according to claim 66 wherein $R^{16}$ is hydrogen, alkylene of 1 to 4 carbon atoms or alkylene of 1 or 2 carbon atoms substituted by phenyl.

68. A method according to claim 50 wherein the compound is of the formula (V):

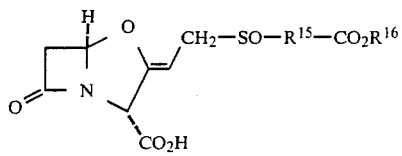 (V)

or a pharmaceutically acceptable salt thereof wherein $R^{15}$ is a divalent hydrocarbon of 1–8 carbon atoms and $R^{16}$ is hydrogen or a hydrocarbon of 1–8 carbon atoms.

69. A method according to claim 50 wherein the compound is of the formula (V):

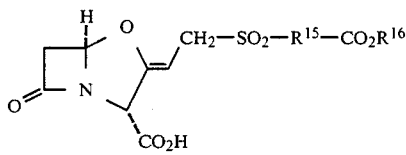 (V)

or a pharmaceutically acceptable salt thereof wherein $R^{15}$ is a divalent hydrocarbon of 1–8 carbon atoms and $R^{16}$ is hydrogen or a hydrocarbon of 1–8 carbon atoms.

70. A method according to claim 50 wherein R is methyl, ethyl, n-propyl, n-butyl, 2-methoxyethyl, 2-benzyloxymethyl, 2-ethoxyethyl, 3-methoxypropyl, benzyl, p-chlorobenzyl, p-methoxybenzyl, m-methoxybenzyl, m-methylbenzyl, phenyl, 4-fluorophenyl or 2-phenylethyl.

71. A method according to claim 50 wherein A is hydrogen or a sodium, potassium, calcium, magnesium, ammonium, alkylamine, dialkylamine, trialkylamine or pyrrolidine ion.

72. A method according to claim 50 wherein A is a pharmaceutically acceptable alkali metal ion.

73. A method according to claim 50 wherein A is a pharmaceutically acceptable alkaline earth metal ion.

74. A method according to claim 50 wherein the compound is in the form of the sodium salt.

75. A method according to claim 50 wherein the compound is in the form of the potassium salt.

76. A method according to claim 50 wherein the compound is in the form of a pharmaceutically acceptable salt in crystalline form.

77. A method according to claim 50 wherein the compound is in the form of an ester wherein the ester is of the formulae

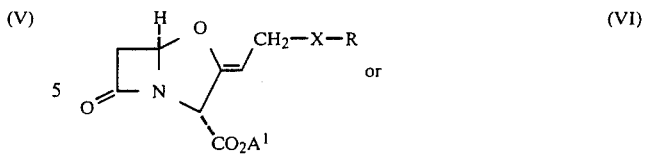 (VI)

or

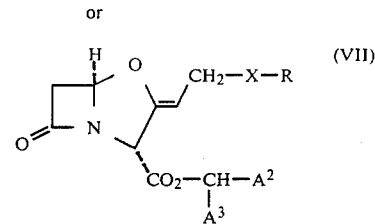 (VII)

wherein X is S, SO or $SO_2$, R is an inert hydrocarbon of up to 20 carbon atoms unsubstituted or substituted by halogen, by a member selected from the group consisting of $OR^1$, $O.COR^1$, $CO.R^1$, $CO_2R^1$, $NHR^1$, $NR^1R^2$, $NH.CO.R^1$, $NR^2CO^1$, $NHCO_2R^1$ and $NR^2CO_2R^1$ wherein $R^1$ is hydrogen or a hydrocarbon of up to 8 carbon atoms and $R^2$ is alkyl of 1 to 3 carbon atoms, or by halogen and a member of said group which will not lead to rapid degradation of the compound of the formula (II), $A^1$ is alkyl of 1 to 8 carbon atoms unsubstituted or substituted by halogen, $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen, $A^5$ or $OA^5$ wherein $A^5$ is alkyl of up to 6 carbon atoms; and $A^3$ is phenyl unsubstituted or substituted by halogen, $A^5$ or $OA^5$ wherein $A^5$ is as above defined.

78. A method according to claim 50 wherein the compound is in the form of the benzyl ester.

79. A method according to claim 50 wherein the compound is in the form of the p-methoxybenzyl ester.

80. A method according to claim 50 wherein the compound is in the form of a hydrogenalyzable ester.

81. A method according to claim 50 wherein the compound of formula (II) or its salt or ester thereof and said penicillin are present in a ratio of 1:10 to 3:1.

82. A method according to claim 81 wherein the ratio is 1:5 to 2:1.

83. A method according to claim 81 wherein the ratio is 1:1 to 1:3.

84. A method according to claim 50 wherein the penicillin is benzylpenicillin.

85. A method according to claim 50 wherein the penicillin is phenoxymethyl penicillin.

86. A method according to claim 50 wherein the penicillin is carbenicillin.

87. A method according to claim 50 wherein the penicillin is methicillin.

88. A method according to claim 50 wherein the penicillin is propicillin.

89. A method according to claim 50 wherein the penicillin is ampicillin.

90. A method according to claim 50 wherein the penicillin is ticarcillin.

91. A method according to claim 50 wherein the penicillin is cyclacillin.

92. A method according to claim 50 wherein the penicillin is epicillin.

93. A method according to claim 50 wherein the administration is oral.

94. A method according to claim 50 wherein the administration is parenteral.

95. A method according to claim 50 wherein the administration is by injection.

96. A method according to claim 50 wherein the administration is by infusion.

97. A method according to claim 50 wherein the penicillin is amoxycillin.

98. A method according to claim 97 wherein the amoxycillin is in the form of a pharmaceutically acceptable salt, a hydrate or an in-vivo hydrolyzable ester.

* * * * *